(12) United States Patent
Oonuki

(10) Patent No.: US 7,819,808 B2
(45) Date of Patent: Oct. 26, 2010

(54) ULTRASOUND IMAGE DIAGNOSIS APPARATUS AND METHOD DISPLAYING A DIASTOLIC AND/OR SYSTOLIC END PERIOD

(75) Inventor: Masato Oonuki, Tochigi-ken (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 971 days.

(21) Appl. No.: 11/399,463

(22) Filed: Apr. 7, 2006

(65) Prior Publication Data

US 2006/0241449 A1    Oct. 26, 2006

(30) Foreign Application Priority Data

Apr. 12, 2005  (JP) .............................. 2005-114265

(51) Int. Cl.
   *A61B 8/00*  (2006.01)
(52) U.S. Cl. ....................................... 600/443; 382/128
(58) Field of Classification Search ................. 600/440, 600/441, 443–450; 73/596, 609, 618–632; 367/138, 178; 382/128, 278, 284
   See application file for complete search history.

(56) References Cited

U.S. PATENT DOCUMENTS

| | | | |
|---|---|---|---|
| 4,271,842 A | 6/1981 | Specht et al. | |
| 5,813,986 A | 9/1998 | Ubukata | |
| 6,350,238 B1 | 2/2002 | Olstad et al. | |
| 6,674,879 B1 | 1/2004 | Weisman et al. | |
| 2003/0016852 A1 | 1/2003 | Kaufman et al. | |
| 2004/0077952 A1 | 4/2004 | Rafter et al. | |
| 2004/0092816 A1 | 5/2004 | Ossmann et al. | |
| 2004/0225219 A1 | 11/2004 | Demers | |
| 2004/0267122 A1 | 12/2004 | Nadadur et al. | |
| 2006/0058623 A1 | 3/2006 | Torp | |

FOREIGN PATENT DOCUMENTS

| | | |
|---|---|---|
| JP | 2-45046 | 2/1990 |
| JP | 3-41938 | 2/1991 |
| JP | 9-140711 | 6/1997 |
| JP | 2001-79006 | 3/2001 |
| JP | 2004-73850 | 3/2004 |

*Primary Examiner*—Ruth S Smith
*Assistant Examiner*—Parikha S Mehta
(74) *Attorney, Agent, or Firm*—Oblon, Spivak, McClelland, Maier & Neustadt, L.L.P.

(57) ABSTRACT

An ultrasound image diagnosis apparatus and an ultrasound image processing method that can automatically display a pair of a cardiac systolic end period image and a cardiac diastolic end period image based on living body signal data. A plurality of ultrasound images are collected from a patient and stored in a memory in correspondence with living body signal data, such as an ECG wave. When a freeze instruction is input during a reproduction of ultrasound images, a pair of images of a cardiac diastolic end period and a systolic end period is searched for going back from the freeze input time. A pair of the diastolic end period image and the systolic end period image is automatically displayed on a screen of the ultrasound image diagnosis apparatus.

30 Claims, 10 Drawing Sheets

ULTRASOUND IMAGE DIAGNOSIS APPARATUS AND METHOD DISPLAYING A DIASTOLIC AND/OR SYSTOLIC END PERIOD

CROSS-REFERENCE TO RELATED APPLICATIONS

This application claims priority from, and the benefit of, Japanese Patent Application No. 2005-114265, filed on Apr. 12, 2005, the contents of which are expressly incorporated herein by reference in their entirety.

BACKGROUND OF THE INVENTION

1. Field of the Invention

The present invention relates to an ultrasound image diagnosis apparatus and an apparatus and method for processing an image display thereof, and more particularly to an ultrasound image diagnosis apparatus and method that can automatically search for a cardiac diastolic end period image and a cardiac systolic end period image, the searched cardiac diastolic end period image appearing just following the searched diastolic end period image, and to display such images in parallel on a screen.

2. Discussion of the Background

An ultrasound image diagnosis apparatus transmits ultrasound through ultrasound transducers installed in an ultrasound probe to an object, such as a patient, and receives reflected ultrasound due to differences of acoustic impedances of the object's organs so as to display the image of the organ on a monitor.

Since an ultrasound image diagnosis apparatus can easily obtain and observe two dimensional images in a real time by simply contacting an ultrasound probe to a patient body surface, it is widely used as an apparatus for diagnosing functions or status of a cardiologic organ, such as a heart in a patient's body.

To diagnose an organ in cardiology, in particular to diagnose functions of a heart, it is usual to make observations comparing two images, one of a diastolic end period that shows the most expanded status of the heart and one of a systolic end period that shows the most contracted status of a patient's heart, respectively. To perform such an image comparison, an observer needs to operate a panel so as to display the diastolic end period image and the systolic end period image on the same screen as a dual display.

Usually, an ultrasound image diagnosis apparatus includes a memory unit for storing obtained ultrasound images, i.e., diagnosis images, through an ultrasound probe in a time series. A plurality of ultrasound images stored in a memory unit can be read out by an optional selection. However, to acquire a dual display of a systolic end period image and an diastolic end period image of a heart, it has been conventional to search for and select a systolic end period image and diastolic end period image among a plurality of images stored in a memory unit. That operation is time and labor consuming for an operator or an inspector.

To diagnose cardiac functions, it has recently been proposed to synchronize ultrasound images with electrocardiogram data obtained through an electrocardiograph. For example, Japanese Patent Application Publication No. 2001-79006 proposes a synchronized displaying method for displaying a B mode image with electrocardiogram data. Japanese Patent Application Publication No. 2004-73850 proposes another method for displaying successive images by synchronizing with electrocardiogram data that is separately obtained from the ultrasound images. Further, Japanese Patent Application Publication No. 2001-344370 proposes a method for measuring corresponded phases of ultrasound images of a cardiac diastolic period and systolic period by detecting a heart cycle.

SUMMARY OF THE INVENTION

However, the present inventors recognized these prior proposals have never intended to automatically display a dual image of a diastolic end period and a systolic end period at an optional heart cycle at all. Thus, the conventional techniques have never disclosed nor suggested to solve the above-mentioned problems for displaying a pair of ultrasound images of a cardiac diastolic period and systolic period that are detected at a desired heart cycle.

As explained above, to diagnose functions of an organ in cardiology, it has been conventional to display and compare a diastolic end period image and a systolic end period image by searching among a plurality of collected images through an ultrasound image diagnosis apparatus. Accordingly, it has been required for an operator of the apparatus to select a pair of the latest diastolic end period image and the latest systolic end period image to display such images as a dual image. To do so, an operator needs to manually freeze image collection and to select a diastolic end period image and a systolic end period image. Until selecting and displaying a pair of the latest diastolic end period image and the latest systolic end period image, an operator must repeat the panel operations of freezing and selecting among many stored images to display desired images at a required form. Accordingly, it has conventionally taken a long time to display a pair of desired images for a comparison. Such operations give a heavy workload to an operator. Further, since it takes a long time to display the desired images, it has been difficult to perform an image diagnosis in a quick time. Thus, the conventional techniques have various problems for performing a speedy image diagnosis.

An object of the present invention is to address the above-noted and other problems. Thus, the present invention provides a novel ultrasound image diagnosis apparatus, a novel image displaying apparatus, and a novel method for automatically displaying a pair of cardiac images of a diastolic end period image and a systolic end period at a desired time point in a heart cycle as a dual display.

To achieve these purposes, an embodiment of the present invention provides a novel ultrasound image diagnosis apparatus including: a transmitting and receiving unit configured to transmit and receive ultrasound to and from an object; a memory unit configured to store a plurality of ultrasound images acquired through the transmission and reception of the ultrasound in correspondence to living body signal data acquired through a living body signal measuring unit; an input unit configured to perform prescribed input operations; a display unit configured to display the plurality of ultrasound images; and a display control unit configured to display each image that corresponds to each of a cardiac diastolic end period and a cardiac systolic end period by reading out the respective ultrasound images from the memory unit based on the living body signal data in accordance with an input of a freeze command through the input unit during a display of the ultrasound image by searching back from an acquisition time of the displayed image at the freeze input time.

Another embodiment of the present invention provides a novel ultrasound image diagnosis apparatus including: a transmitting and receiving unit configured to transmit and receive ultrasound to and from an object; a memory unit configured to store a plurality of ultrasound images acquired through the transmission and reception of the ultrasound relating to living body signal data acquired through a living body signal measuring unit; an input unit configured to perform prescribed input operations; a display unit configured to display the plurality of ultrasound images; and a display control unit configured to display each image that corresponds to each of a cardiac diastolic end period and a cardiac systolic end period by reading out the respective ultrasound images from the memory unit based on the living body signal data in accordance with an input of a freeze command through the input unit during a display of the ultrasound image by searching back from an acquisition time of the displayed image at the freeze input time, wherein the latest diastolic end period is detected by searching back from a timing of the freeze input, and the latest systolic end period is detected just prior to the latest diastolic end period.

Another embodiment of the present invention provides a novel image display apparatus including: a reading unit configured to read ultrasound images including a plurality of frames and living body signal data; a memory configured to store the read ultrasound images with a correspondence to the living body signal data; an input unit configured to operate a prescribed operation including a freeze input; a display unit configured to display the images; and a display control unit configured to search for each of image frames corresponding to each of the latest cardiac systolic end period and the latest diastolic end period in the memory by searching back on the living body signal data from a time point of the freeze input to display the searched images of the systolic end period and the diastolic end period on the display.

Another embodiment of the present invention provides a novel method for processing ultrasound image display comprising: transmitting and receiving ultrasound; measuring living body signals; storing a plurality of image frames collected by the transmission and reception with a correspondence to living body signal data collected by the measuring; inputting a freeze input; searching for a cardiac systolic end period image or a cardiac diastolic end period image based on the living body signal data by searching back from a time of the freeze input; and displaying the searched cardiac systolic end period image or the searched cardiac diastolic end period image on a screen.

Another embodiment of the present invention provides a novel method for processing ultrasound image display including: transmitting and receiving ultrasound; measuring living body signals; storing a plurality of image frames collected by the transmission and reception with a correspondence to living body signal data collected by the measuring; inputting a freeze input; searching for a cardiac systolic end period image or a cardiac diastolic end period image based on the living body signal data by searching back from a time of the freeze input; and displaying the searched cardiac systolic end period image or the searched cardiac diastolic end period image on a screen, wherein the latest cardiac systolic end period image and the latest cardiac diastolic end period image are displayed as a dual display.

According to embodiments of the present invention, it becomes possible to rapidly search for and to display a patient's cardiac images of a diastolic end period and a systolic end period as a dual image to observe variations of the images in each of heart cycles. Further it becomes possible to efficiently operate for performing a speedy and easy image diagnosis.

BRIEF DESCRIPTION OF THE DRAWINGS

The accompanying drawings, which are incorporated in and constitute part of this specification, illustrate various embodiments and/or features of the present invention, and together with the description, serve to explain embodiments of the present invention. Where possible, the same reference number are used throughout the drawings to describe the same or like parts. In the drawings.

DESCRIPTION OF THE PREFERRED EMBODIMENTS

Figure 1:
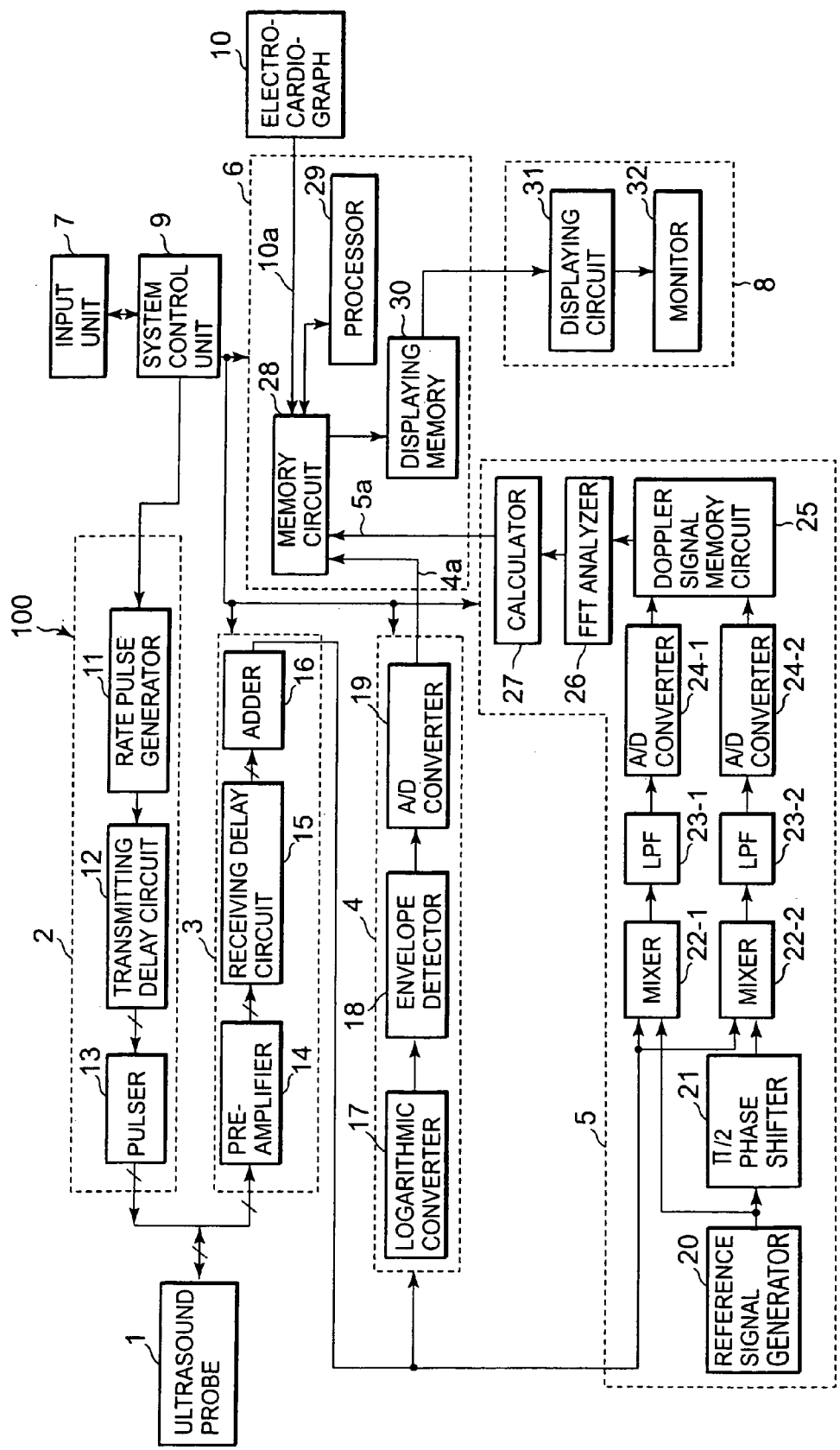
FIG. 1 is a block diagram illustrating an entire construction of an ultrasound image diagnosis apparatus of a first embodiment according to the present invention.

With reference to the drawings, the embodiments of an ultrasound image diagnosis apparatus and method consistent with the present invention are explained. FIG. 1 is a block diagram for illustrating an entire construction of an embodiment of the ultrasound diagnostic apparatus consistent with the present invention.

As illustrated in FIG. 1, the ultrasound image diagnosis apparatus 100 includes an ultrasound probe 1 for transmitting ultrasound to a patient body and receiving echo signals reflected from the patient body by being placed in contact with a patient body surface, an ultrasound transmitting unit 2 for transmitting ultrasound, an ultrasound receiving unit 3 for receiving echo signals as received signals, a B mode processing unit 4 and a Doppler mode processing unit 5 for respectively processing the received signals, an image processing unit 6 for executing image processing operations, an input unit 7 for inputting image selection data, a display unit 8 for displaying images, and a system control unit 9 for controlling operation of the apparatus. The ultrasound image diagnosis apparatus 100 consistent with the present invention can use data of an electrocardiograph 10.

The ultrasound probe 1 is constructed in a small and light body and includes a plurality of minute ultrasound transducers provided on a forward edge portion of the probe. The ultrasound transducers convert electric pulses to ultrasound pulses at a transmitting time and convert ultrasound reflection signals to electric received signals. The possible types of ultrasound probes include, as examples, a sector scan type, a linear scan type, and a convex scan type. In accordance with a diagnostic portion, an appropriate type is selected. In the following embodiments, it is assumed that a sector scan type ultrasound probe is used in the apparatus. The ultrasound probe 1 is coupled to an ultrasound transmitting unit 2 and an ultrasound receiving unit 3 through a cable.

Ultrasound transmitting unit 2 generates ultrasound driving signals. The ultrasound transmitting unit 2 includes a rate pulse generator 11 for deciding a repeating period of an ultrasound heart cycle for radiating into an object, a transmitting delay circuit 12 for deciding a focusing distance and a deflection angle of a transmitting ultrasound beam, and a pulser 13 for generating high voltage pulses for driving ultrasound transducers. Transmitting delay circuit 12 includes a plurality of independent delaying circuits of the same number as the ultrasound transducers in the ultrasound probe 1 and decides a driving timing of the plurality of ultrasound transducers. Transmitting delay circuit 12 affords a focusing delay time for focusing ultrasound into a prescribed depth and a transmitting delay time for deflecting ultrasound in a prescribed direction to rate pulses. Pulser 13 includes, similar to the transmitting delay circuit 12, a plurality of independent driving circuits of the same number as the ultrasound transducers for driving the ultrasound transducers in the ultrasound probe 1, and pulser 13 generates driving pulses for radiating ultrasound.

Ultrasound receiving unit 3 receives ultrasound echo signals reflected from an object. The ultrasound receiving unit 3 includes a pre-amplifier 14 for amplifying weak signals converted through the ultrasound transducers so as to maintain a sufficient S/N (signal to noise) ratio, a receiving delay circuit 15 for affording a focusing delay time to output signals of the pre-amplifier 14 in a predetermined direction for focusing ultrasound to acquire a fine width of a receiving beam, and an adder 16 for collecting the received plurality of signals from the ultrasound transducers by adding.

The collected receiving signals added by adder 16 are processed for B mode imaging signals. The B mode processing unit 4 includes logarithmic converter 17 for performing an amplitude compression through logarithmic conversion of received signals input from the adder 16 to emphasize weak signals, an envelope detector 18 for detecting an envelope of the logarithmic converted received signals by removing an ultrasound frequency component to detect amplitude only, and an A/D converter 19 for generating B mode signals by performing A/D conversion of output signals from the envelope detector 18. Since received signals from an object generally have an amplitude of a wide dynamic range over 80 dB, an amplitude compression needs to be performed to display the images on a normal television monitor that has a small dynamic range.

B mode processing unit 4 successively outputs B mode images and constructs 1 frame of a B mode ultrasound image. The B mode ultrasound image obtained through ultrasound transmission and reception during one optional time period includes a plurality of B mode image frames.

Doppler mode processing unit 5 performs signal processing for a color Doppler image or an organ Doppler image. Doppler mode processing unit 5 includes a reference signal generator 20, a $\pi/2$ phase shifter 21, first and second mixers 22-1 and 22-2, first and second low pass filters (LPFs) 23-1 and 23-2, A/D converters 24-1 and 24-2, a Doppler signal memory circuit 25, a FFT (Fast Fourier Transformation) analyzer 26, and a calculation unit 27. Doppler mode processing unit 5 mainly performs orthogonal phase detection and FFT analyzing.

Echo signals from adder 16 are supplied to each first input terminal of the first and second mixers 22-1 and 22-2. An output from the reference signal generator 20 that has a similar frequency of the echo signals is directly input to a second input terminal of the first mixer 22-1. Similarly, the output from reference signal generator 20 is supplied to a second input terminal of the second mixer 22-2 after shifting its phase by 90 degrees. The respective outputs from the first and second mixers 22-1 and 22-2 are supplied to each of the first and second low pass filters 23-1 and 23-2. The low pass filter 23-1 excludes a sum component of a frequency of signals input from the adder 16 and a frequency of the reference signal generator 20 and extracts a difference component only. The second low pass filter 23-2 excludes a sum component of a frequency of signals input from the adder 16 and a frequency of output signal from the $\pi/2$ phase shifter 21 and extracts a difference component only.

The respective outputs from the first and second low pass filters 23-1 and 23-2 are converted to digital signals through the first and second A/D converters 24-1 and 24-2, respectively. The digitally converted output signals from the A/D converters 24-1 and 24-2 are first stored in Doppler signal memory circuit 25 and then supplied to the FFT analyzer 26. The calculator 27 calculates a center or a width of a spectrum obtained through the FFT analyzer 26.

Each Doppler mode image successively obtained from the Doppler mode processing unit 5 constructs frames of a plurality of color Doppler mode images and organ Doppler images.

The present invention is applicable to either one or both of B mode image data or Doppler mode image data. Thus, the image of the present invention can be applicable to either one or both of a B mode image or a Doppler mode image. Accordingly, the following image or image data are simply explained as an "ultrasound image data" without distinguishing whether the image is B mode ultrasound image data or Doppler mode ultrasound image data. Similarly, both of B mode ultrasound image frame data and Doppler mode ultrasound image frame data are simply referred to as "image frame data".

Image processing unit 6 includes a memory circuit 28, a processor 29, and a displaying memory 30. The memory circuit 28 stores ultrasound image 4a obtained in B mode processing unit 4 and/or ultrasound image 5a obtained through Doppler mode processing unit 5 together with electrocardiogram data 10a from an electrocardiograph 10. Thus, ultrasound images 4a and/or 5a from A/D converter 19 and/or calculator 27 have prescribed processing performed in processor 29 and are then stored in memory circuit 28 together with related electrocardiogram data 10a. For example, frame images 4a and/or 5a for each of frames are stored with a relation to a time point on a time series of electrocardiogram data 10a. It is also possible to store just time points corresponding to each of a cardiac diastolic end period a cardiac systolic end period based on electrocardiogram data 10a and frame images corresponding to the time points. As to images corresponding to other time points, it is possible to store such images without relating to the electrocardiogram data 10a.

Processor 29 in the image processing unit 6 reads out ultrasound image data and electrocardiogram data stored from the memory circuit 28 and judges each of a cardiac diastolic end period and a systolic end period based on a timing synchronized relationship between ultrasound transmission and reception of ultrasound images and the electrocardiogram data. Thus, each of a cardiac diastolic end period and a systolic end period are judged based on electrocardiogram data and each of frame data (images) corresponding to the diastolic end period and systolic end period are extracted. The extracted frame data (images) corresponding to each of the diastolic end period and systolic end period are stored in the memory circuit 28.

Displaying memory 30 in the image processing unit 6 stores ultrasound image data and electrocardiogram data to be displayed in the display unit 8. Ultrasound images obtained in a real time are first stored in display memory 30 through the memory circuit 28 and are then displayed in the display unit 8.

Input unit 7 includes an operation panel for inputting data of an object and radiographic conditions by using input devices, such as a keyboard, a track ball, a mouse, etc. Through the input unit 7, operation can be performed for instructing a static (freeze) display at an optional image among moving image displays of ultrasound images, for instructing to display images corresponding to each of a diastolic end period and a systolic end period, and for instructing other prescribed input operations.

Display unit 8 includes a displaying circuit 31 and a monitor 32. Ultrasound images and electrocardiogram data stored in the displaying memory 30 in the image processing unit 6 have D/A conversion performed thereon, and then undergo a television format conversion at the display circuit 31 in the display unit 8 to be displayed on a monitor 32.

System control unit 9 includes a CPU (Central Processing Unit, not shown) and a memory circuit (not shown). System control unit 9 controls all the operations of each of the units in the ultrasound image diagnosis apparatus 100 in accordance with each of input instructions through the input unit 7. Input unit 7 supplies input data from an operator to the CPU in the system control unit 9. Memory circuit 28 in the image processing unit 6 stores various control data for setting the apparatus and radiation condition input through the input unit 7.

Electrocardiograph 10 measures an electrocardiogram of an object. The measured electrocardiogram data 10a is given a time relationship to an ultrasound image. It is also possible to achieve the time relationship by synchronizing ultrasound transmission and reception through the ultrasound probe 1 with measurement by the electrocardiograph 10. It is further possible to achieve the time relationship by optionally recognizing a common timing between ultrasound transmission and reception of the probe and measurement of the electrocardiograph through the processor 29 at a later time.

Electrocardiograph 10 can be provided independently from the ultrasound image diagnosis apparatus consistent with the present invention so as to be connected through a prescribed interface (not shown). It is also possible to provide it in the ultrasound image diagnosis apparatus. It is further possible to use other vital signals measured by another measuring apparatus, such as VCG (Vector Cardiogram) signals of blood current speeds or organ motion signals in lieu of electrocardiogram data measured by the electrocardiograph 10. It may be desirable to include another vital signal data into the electrocardiogram data.

Figure 2:
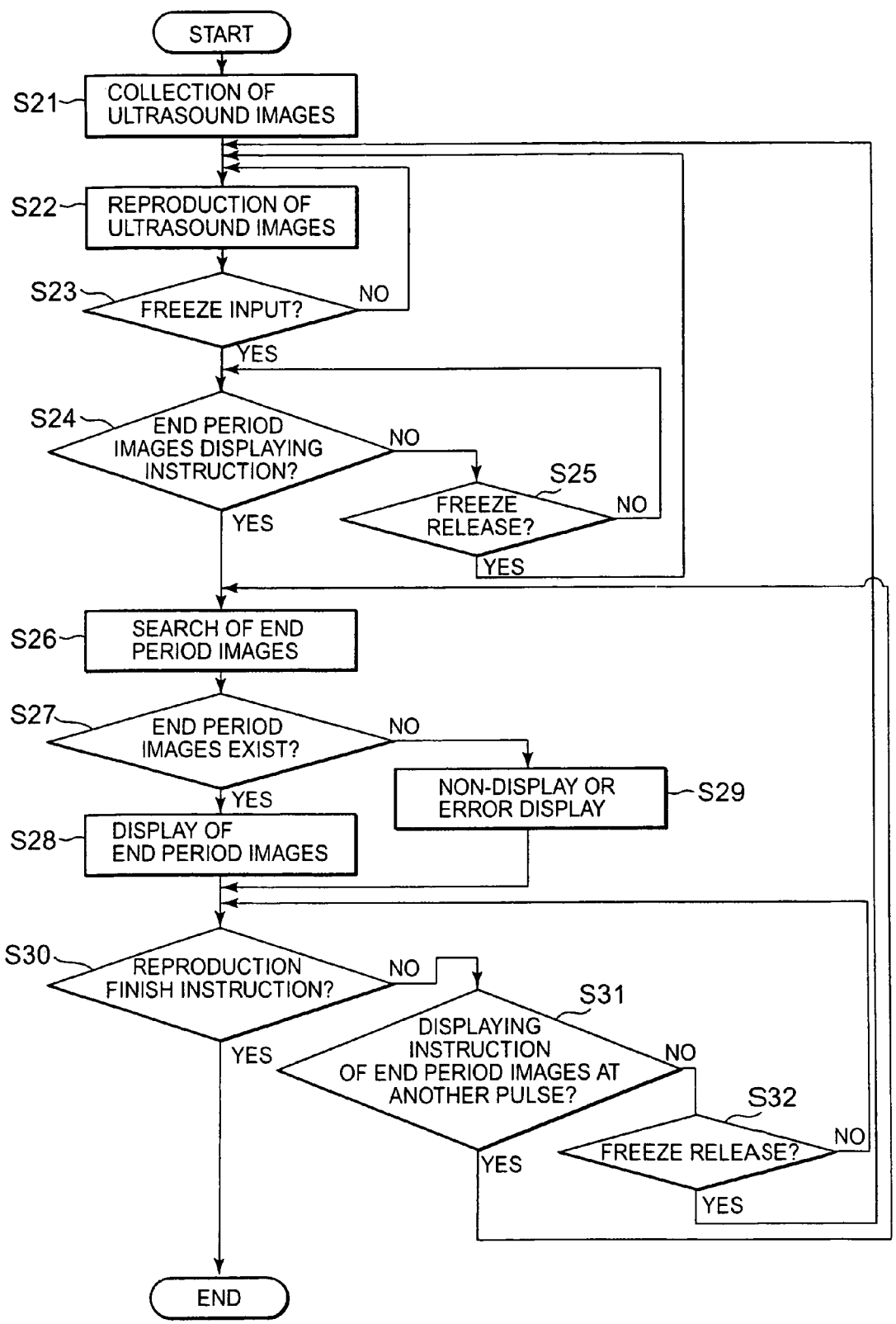
FIG. 2 is a flowchart representing an image displaying method of one embodiment used in the ultrasound image diagnosis apparatus consistent with the present invention.

FIG. 2 illustrates an embodiment process for displaying frame images of a diastolic end period and a systolic end period. FIG. 2 is a flowchart illustrating an embodiment of an image displaying method for the ultrasound image diagnosis apparatus consistent with the present invention.

Figure 3:
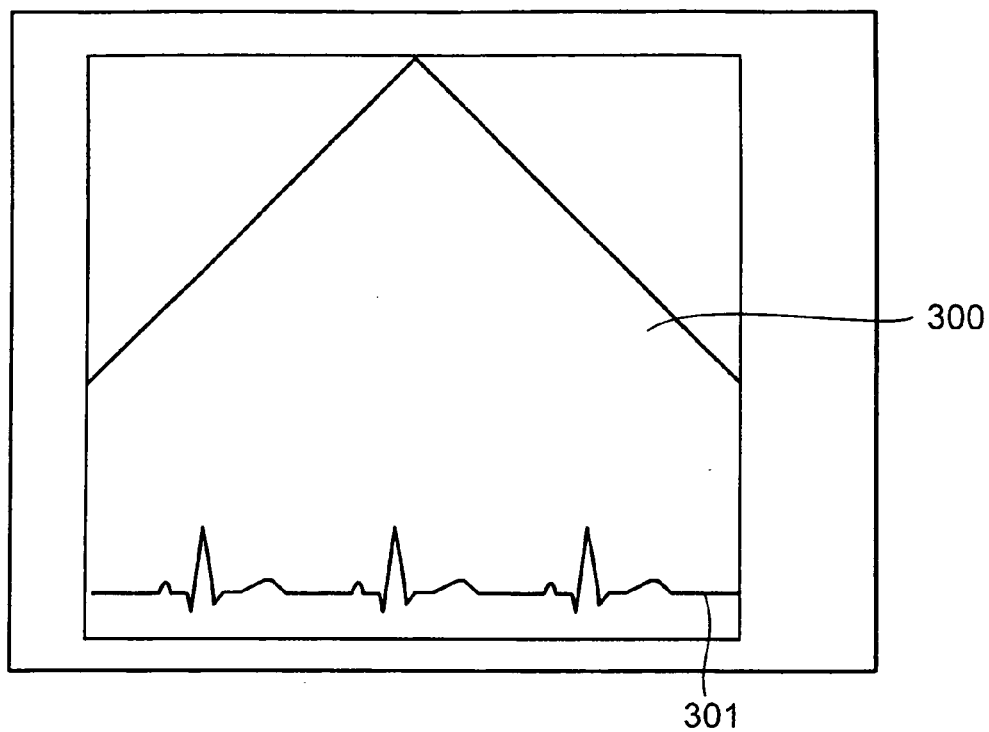
FIG. 3 illustrates an example image of a normal static image at an inspection time.

The ultrasound image diagnosis apparatus shown in FIG. 1 collects cardiac ultrasound image data of an object and the collected image data is stored in the memory circuit 28 (step S21). To observe the stored image data, the stored ultrasound image is reproduced and displayed on the display unit 8 through an operation of the input unit 7 (step S22). Image reproduction is displayed as successive moving images during a contacting period of the ultrasound probe 1 to the object. During this reproduction of images, if no diastolic end period image nor systolic end period image exists, the reproduction of the stored ultrasound image data is continued, if there is no input of an operation of a freeze input through the input unit 7 (step S23, NO), and the operation then returns to step S22. If a diastolic end period image or a systolic end period image exists during image reproduction, a freeze input may be input through the input unit 7 (step S23, YES). The freeze input is then recognized in the system control unit 9, and a frame image corresponding to the timing of the freeze input is displayed on the display unit 8 as a repose image under a control of the system control unit 9. The repose image is, for exemplary as shown in FIG. 3, an ultrasound image 300 displayed together with an electrocardiogram 301.

During this display of the repose image, if no instruction for displaying a diastolic end period image or a systolic end period image is input through the input unit 7 (step S24, NO), a freeze release instruction is input through the input unit 7 (step S25, YES). Then, the repose image display is released and reproduction of ultrasound images is restarted in step S22. On the contrary, if no freeze release is instructed through the input unit 7 (step S25, NO), an end period images displaying instruction for the displayed repose image is again executed (step S24).

When an instruction for displaying a diastolic end period image and a systolic end period image is input through the input unit 7 (step S24, YES), the input of an end period images displaying instruction is recognized in the system control unit 9. In accordance with the recognition, the image processing unit 6 searches for the latest diastolic end period image and the latest systolic end period image by searching back or "ascending" from the timing of the freeze input at step S23 (step S26). Thus, a search of end period images is performed for whether the latest diastolic end period image and the latest systolic end period image exist in the memory circuit 28 by searching back or "ascending" from a position of the image frame of the currently displayed repose image (step S26).

A search of end period images is performed based on ultrasound image data and electrocardiogram data stored in the memory circuit 28 of the image processing unit 6. For example, a timing of a freeze input or a time point corresponded to a frame of a displayed repose image is judged on the electrocardiogram data 10a. and the respective time points of the latest images of a diastolic end period and a systolic end period are judged by searching back from that time point. After judging the time points of the diastolic end period and systolic end period, it is judged whether or not the end period images corresponded to the time point exist (step S27). If the end period images corresponded to the time point exist (step S27, YES), a diastolic end period image corresponded to the diastolic end period time point and a systolic end period image corresponded to the systolic end period time point are read out from the memory circuit 28 in the image processing unit 6. The read out diastolic end period image and systolic end period image are then displayed on the display unit 8 through the displaying memory 30 (step S28).

Figure 4:
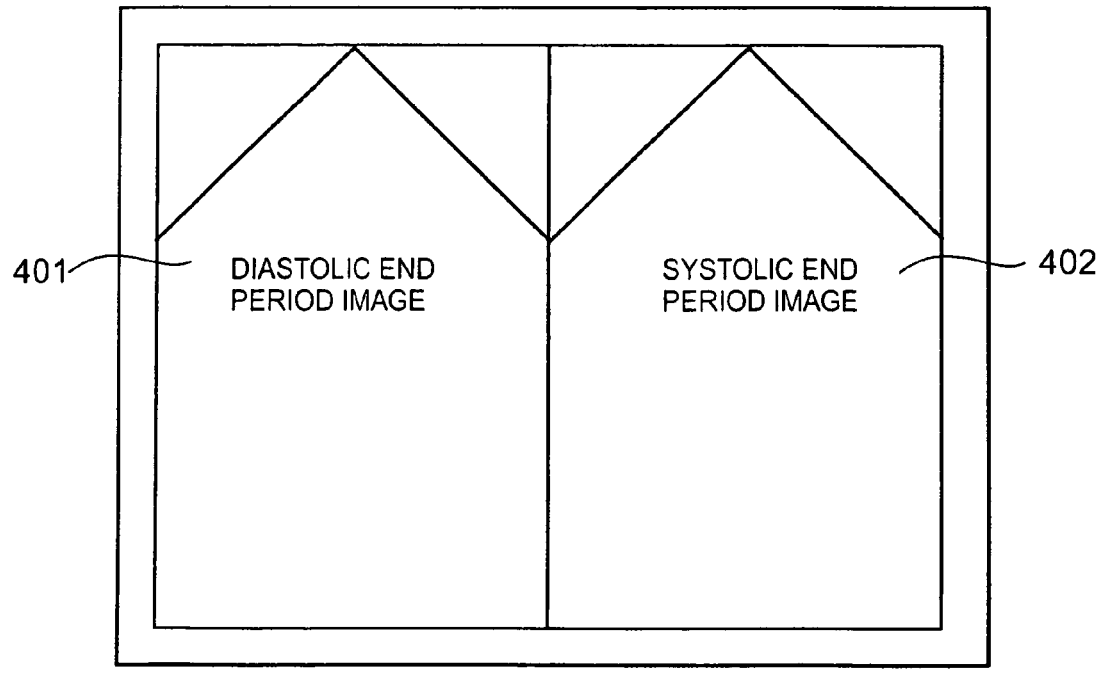
FIG. 4 illustrates an example display of images of a diastolic end period and a systolic end period.

FIG. 4 illustrates an exemplary dual display of a diastolic end period image and a systolic end period image. As shown in FIG. 4, a diastolic end period image 401 and a systolic end period image 402 are displayed in parallel on left and right sides.

Figure 5:
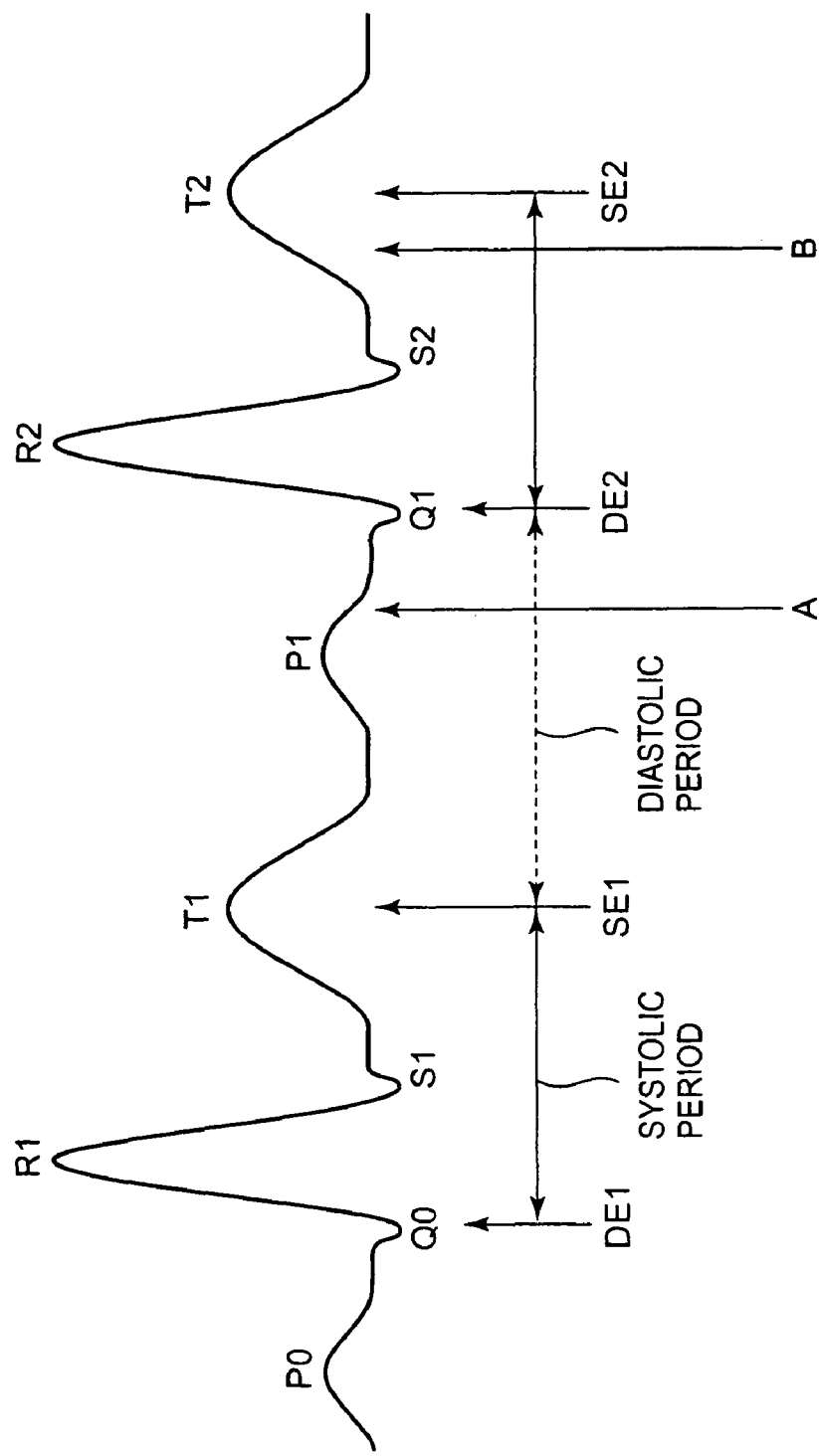
FIG. 5 illustrates an example of a typical electrocardiogram.

FIG. 5 illustrates a typical exemplary of an electrocardiogram. Generally, heart cycle calculation is performed based on an R wave or an R-R interval between an R wave and a next R wave on an electrocardiogram. According to the present embodiment, a diastolic end period and a systolic end period located in a P-Q-R-S-T area that includes an R-R interval on the electrocardiogram are considered as a pair. In FIG. 5, P0 and P1 indicate P waves, Q0 and Q1 show Q waves, R1 and R2 show R waves, S1 and S2 indicate S waves, and T1 and T2 indicate T waves. In FIG. 5, an interval between R1 and R2 shows the R-R interval. A cardiac systolic period is an interval between a Q0 wave appearing at time DE1 and a Q1 wave appearing at time SE1. A cardiac diastolic period is an interval between a T1 wave appearing at time SE1 and a Q1 wave appearing at time DE2. Thus, the respective DE1 and DE2 are time points for indicating a diastolic end period, and the respective SE1 and SE2 are time points for indicating a systolic end period.

In an exemplary electrocardiogram illustrated in FIG. 5, the respective end period images corresponded to the diastolic end period DE1 and the systolic end period SE1 are dually displayed as one pair. For example, if a timing of the freeze input at step S23 in FIG. 2 or a time point corresponded to the image frame of a repose image displayed by a freeze input is located at a point A as shown in FIG. 5, by searching back from a timing of the freeze input, two images corresponded to the respective time points of a diastolic end period DE1 and a systolic end period SE1 are displayed as the latest diastolic end period image and the latest systolic end period image, respectively. If a time point of a freeze input is located at a point B as shown in FIG. 5, since the point B is located prior to a time point of a systolic end period SE2 that forms a pair with a diastolic end period DE2, no pair of images exist. Consequently, the dual display of a diastolic end period image and a systolic end period image at this timing also becomes images corresponded to each of time points of the diastolic end period DE1 and the systolic end period SE1, i.e., the latest complete pair.

At a time point B, if necessary, it is also possible to display two images corresponded to each of time points of a systolic end period SE1 and diastolic end period DE2 as a systolic end period image and a diastolic end period image, respectively.

Turning to step S27 in FIG. 2, if it is judged that no applicable diastolic end period image and systolic end period image exist (step S27, NO), a diastolic end period image and a systolic end period image are not displayed or an error message indicating that no existence of a desired diastolic end period image and a systolic end period image is displayed (step S29).

At step S28, if an instruction for finishing reproduction of end period images is input during a display of end period images through the input unit 7 (step S30, YES), the system control unit 9 performs a control so as to finish reproduction of end period images.

When an instruction for finishing reproduction of end period images is not input (step S30, NO), but another instruction is input for displaying end period images at another heart cycle (step S31, YES), the process goes back to the search of end period images of step S26, and performs searching of a diastolic end period image and a systolic end period image at another heart cycle based on a prescribed setting or the input. Then, each step as explained above is followed.

As another heart cycle, for example, if a "1 heart cycle" setting is preliminarily set, a dual display of a diastolic end period image and a systolic end period image at another heart cycle of frame images corresponded to each of a diastolic end period and a systolic end period at 1 heart cycle prior to the heart cycle for displaying the end period images is displayed at step S28. If the input operation for instructing a display of end period images at another heart cycle is repeated, the processes of step S31 and steps S26 to S30 are repeated. Thus, by searching back each 1 heart cycle, an image display of a diastolic end period and a systolic end period belonging at each heart cycle is repeated. It is also possible once searching back or "ascending" several heart cycles to a specific heart cycle to search in a return direction from the specific heart cycle. Hereinafter, to simplify the explanation, the term "searching back" or "ascending" includes both the meaning of simply searching back or "ascending" in one direction, and once reaching a specific heart cycle searching in a return back in an opposite direction.

The prescribed number of heart cycles is not limited to such a 1 heart cycle as the example, but can optionally be set to a number of heart cycles. Further, it is also possible to change the number of heart cycles during a display of end period images based on judgment of an operator, if necessary.

It is also possible to input a desired practical heart cycle number at step S31. Further, it is possible to select a switch, a button, or an icon that is provided to preliminarily input a prescribed heart cycle.

At step 31, when an instruction for displaying end period images at another heart cycle is not input (step S31, NO), the system control unit 9 judges whether or not the freeze should be release (step S32). If a freeze release is judged (step S32, YES), a successive display of ultrasound images is restarted (step S22). If a freeze is not released (step S32, NO), the process returns to step S30 to judge whether an instruction for finishing reproduction exists (step S30).

According to the above explained embodiment, it becomes possible to rapidly display a pair of the latest diastolic end period image and the latest systolic end period image by a simple operation without taking a long time due to complicated operations as in the conventional apparatus and method. Such operations in the present invention can largely eliminate a burden for an operator. Consequently, an operator can concentrate on diagnosis or observing images. The operations of the present invention thereby contribute to increased accuracy of a diagnosis and/or an efficiency of a diagnosis.

According to this embodiment, it becomes possible to display a pair of images of a diastolic end period and a systolic end period at a previous heart cycle by a simple input operation. Since it can perform an image comparison at any optional time, an accuracy of diagnosis can be increased. Further, it becomes possible to display not only the latest diastolic end period image and the latest systolic end period image but also any optional past pair of images without a large burden in displaying them. Thus, the displaying operation can be performed with reduced burdens for an operator.

A method for processing an ultrasound image display consistent with the present invention is not limited to the process illustrated in FIG. 2. As explained in the following embodiments, it is possible to return to a normal repose image display from the display of end period images.

Figure 6:
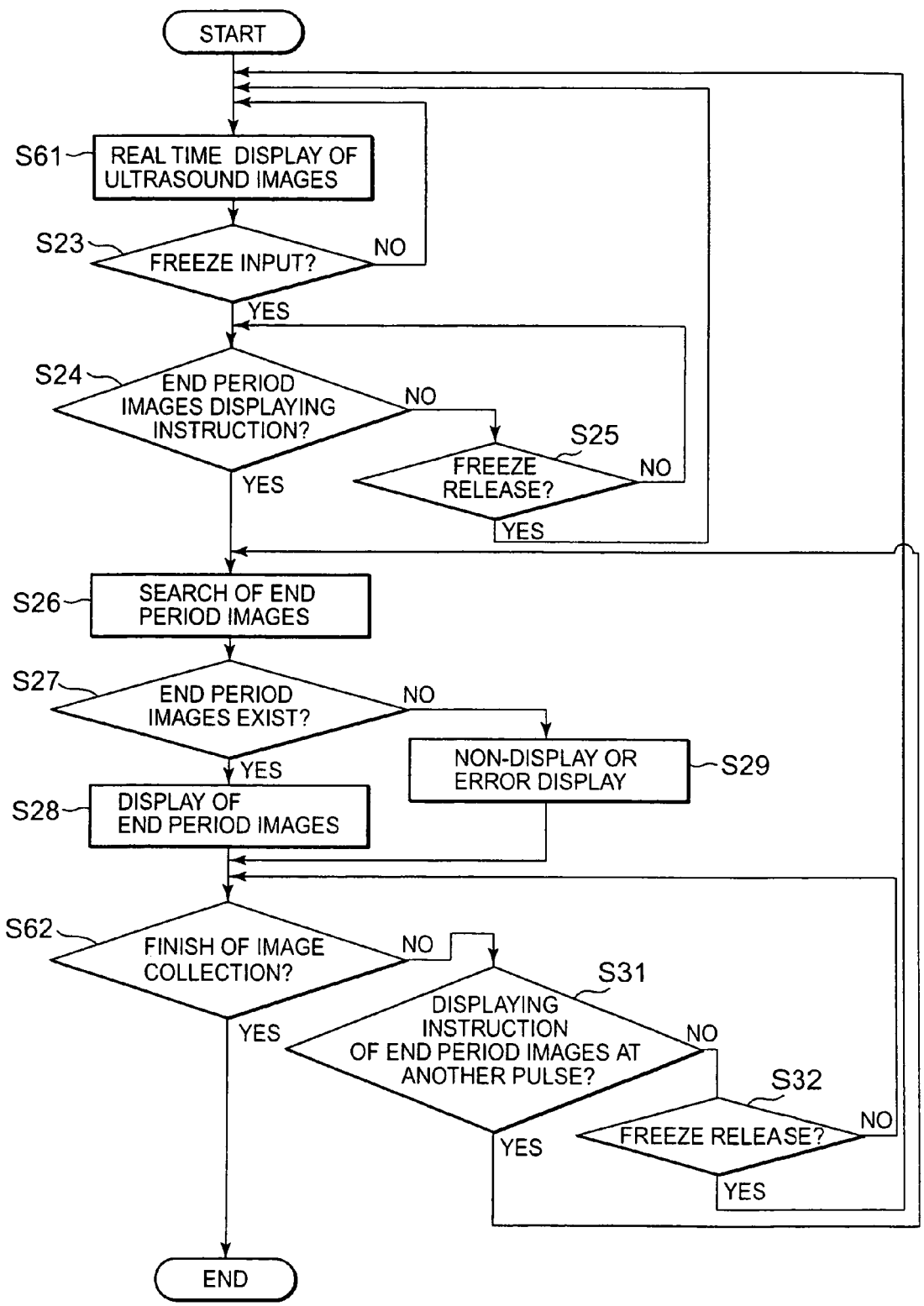
FIG. 6 is a flowchart representing an image displaying method of another embodiment used in the ultrasound image diagnosis apparatus consistent with the present invention.
Figure 7:
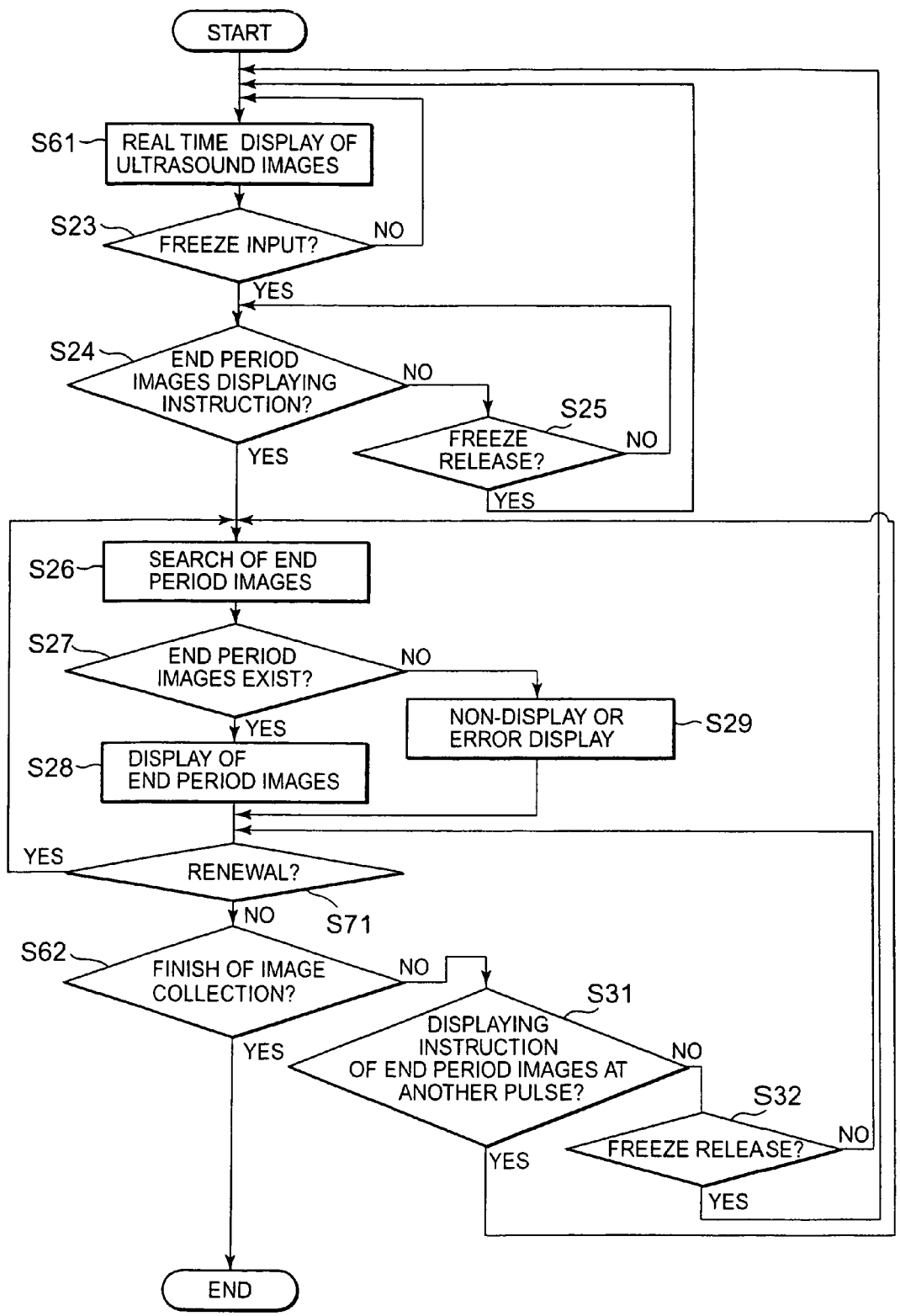
FIG. 7 is a flowchart representing an image displaying method of a further embodiment used in the ultrasound image diagnosis apparatus consistent with the present invention.
Figure 8:
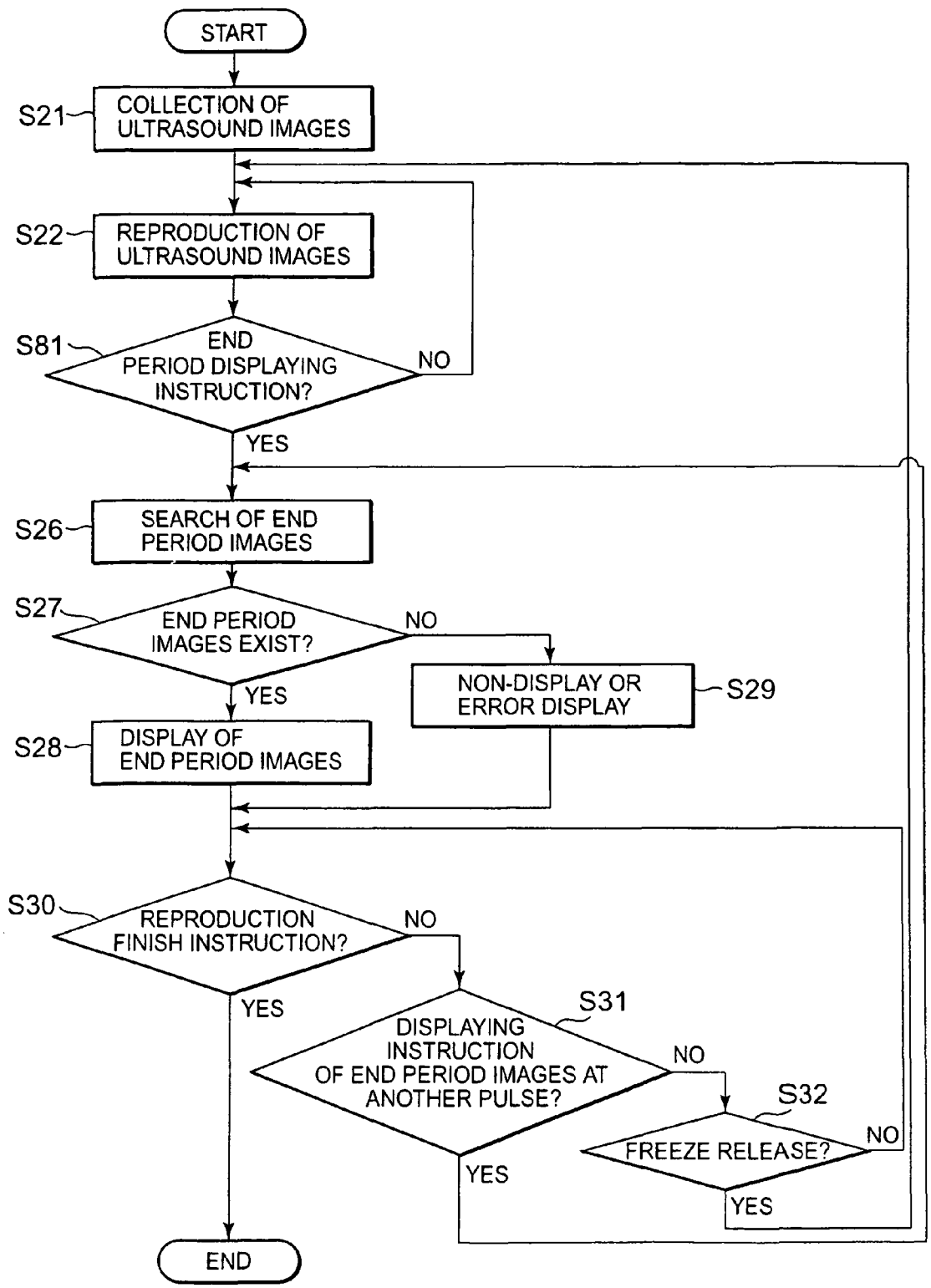
FIG. 8 is a flowchart representing an image displaying method of a still further embodiment used in the ultrasound image diagnosis apparatus consistent with the present invention.

FIGS. 6-8 illustrate other embodiments of image display controlling methods consistent with the present invention.

FIG. 6 is a flowchart showing another embodiment of an image display processing method for an ultrasound image diagnosis apparatus consistent with the present invention. In FIG. 6, steps S23 to S29 and steps S31 and S32 are similar to the steps shown in FIG. 2 with the same reference numbers. For an easier understanding, the same redundant explanations are omitted.

In the embodiment shown in FIG. 2, ultrasound images are reproduced after finishing collection of images. In the embodiment shown in FIG. 6, a pair of a diastolic end period image and a systolic end period image is displayed during a display of collecting ultrasound images in real time.

For an ultrasound diagnosis, cardiac ultrasound images of an object are collected through an ultrasound image diagnosis apparatus as shown in FIG. 1. The collected images are stored in a memory circuit 28. Simultaneously, the collected ultrasound images are displayed on a display unit 8 in a substantial real time (step S61).

During a contacting time of an ultrasound probe 1 to an object, continuous moving images are displayed in real time. During the real time image display, if no freeze input is given through an input unit 7 (step S23, NO), the real time display of collecting ultrasound images is continued. If a freeze input is given (step S23, YES), a system control unit 9 recognizes the freeze input.

System control unit 9 controls an image processing unit 6 so as to display an image frame corresponded to a timing of the freeze input on a display unit 8 as a static image. Even during a period of a display of the static image, collected ultrasound images are stored in the memory circuit 28 so far as the ultrasound probe 1 is still in contact with the object.

During the display of the static image, if no instruction input for displaying a pair of a diastolic end period image and a systolic end period image is given (step S24, NO), a freeze release is input (step S25, YES) for releasing the static image display and for returning to a continuous moving image display. If a freeze release input is not given (step S25, NO), the static image display is continued.

If a dual display instruction of a diastolic end period image and a systolic end period image is input through an input unit 7 (step S24, YES), similar to the process shown in FIG. 2, processes of steps S26 to S29 are performed.

By finishing collection of ultrasound images (step S62), the process of FIG. 6 ends. If collection of images does not finish, similar to the embodiment in FIG. 2, processes of steps S31 and S32 are performed.

Thus, similar to the embodiment in FIG. 2, even when ultrasound images are displayed in a real time display, it becomes possible to display a pair of a diastolic end period image and a systolic end period image at a desired time for achieving comparison of the images.

In the embodiment in FIG. 6, the process ends at a finish of collection of ultrasound images. However, even when an ultrasound probe 1 is detached from an object, it is also possible to display a diastolic end period image and a systolic end period image that belong to a past heart cycle. Thus, even if ultrasound image collection itself is finished, images from a past heart cycle can be displayed based on steps S31 and S32.

FIG. 7 is a flowchart showing another embodiment of a display processing method for an ultrasound image diagnosis apparatus consistent the present invention. In this embodiment, a step S71 is added to the display processing method explained in FIG. 6. Similar to the embodiments of FIGS. 2 and 6, the same numbered steps have the same above-discussed operations, respectively.

In FIG. 7, when a diastolic end period image and a systolic end period image are displayed (step S28), or when no image display or a prescribed error display is noted (step S29), by inputting an instruction of display renewal of a diastolic end period image and a systolic end period image (step S71, YES), the process goes back to the end period images searching step S26.

As explained above, during the dual displaying period of a diastolic end period image and a systolic end period image, ultrasound image collection is continued by contacting an ultrasound probe 1 to an object. Even when an ultrasound probe 1 is detached from an object surface to display a diastolic end period image and a systolic end period image, ultrasound image collection is again started by contacting the probe to the object. At step S71, when a renewal instruction of dual display of a diastolic end period image and a systolic end period image is input, the renewal input is recognized in the system control unit 9.

In accordance with the recognition in system control unit 9, the image processing unit 6 again searches for the latest pair of images of a diastolic end period and a systolic end period by searching going back from a timing of the renewal input at step S71. Thus, a search for finding a pair of the latest diastolic end period image and the latest systolic end period image is executed in the memory circuit 28 by searching going back from a position of the image frame that is currently displayed as a static image (step S26).

Similar to the operation in FIG. 2, the following steps from step S27 are performed and the renewed latest diastolic end period image and systolic end period image are displayed on a display unit 8

Thus, the operation in FIG. 7 can display a pair of the latest diastolic end period image and systolic end period image during collection of ultrasound images at a time of the input operation without once returning to an image display in a real time. Consequently, it becomes possible for an operator to flexibly perform display operations and an operation for diagnosis can be improved.

FIG. 8 is a flowchart illustrating another modification of the display processing method for the ultrasound image diagnosis apparatus consistent with the present invention. In FIG. 8, steps S21, S22 and steps S26 to S32 are similar to steps shown in FIG. 2. To avoid repeating the same explanation, the same steps as in FIG. 2 are not again described.

After finishing ultrasound image collection (step S21), if a dual display of a diastolic end period image and a systolic end period image is desired in a reproduction of the collected images (step S22), as shown in FIG. 8, it is possible to directly instruct to display a diastolic end period image and a systolic end period image from an input unit 7 without inputting a freeze input for temporally stopping reproduction of images (step S81). By inputting this display instruction, continuous reproduction of ultrasound images is substantially ceased.

The input of a display instruction at step S81 is recognized in system control unit 9, and image processing unit 6 performs the steps following step S26 so as to display a diastolic end period image and a systolic end period image that respectively correspond to the latest diastolic end period and systolic end period by searching going back from a timing point for instructing display of a diastolic end period image and a systolic end period image.

In the embodiment shown in FIG. 8, if a diastolic end period image and a systolic end period image are initially desired, a static image need not be first displayed. Accordingly, the operation in FIG. 8 can reduce a burden of an operator and also possibly shorten an operation time for displaying a diastolic end period image and a systolic end period image.

In lieu of steps S23 to S25 in FIG. 6, step S81 in FIG. 8 can be used for achieving the same effect during a display of ultrasound images in a real time.

FIGS. 9-12 illustrate various display manners for a dual display of a diastolic end period image and a systolic end period image.

Figure 9:
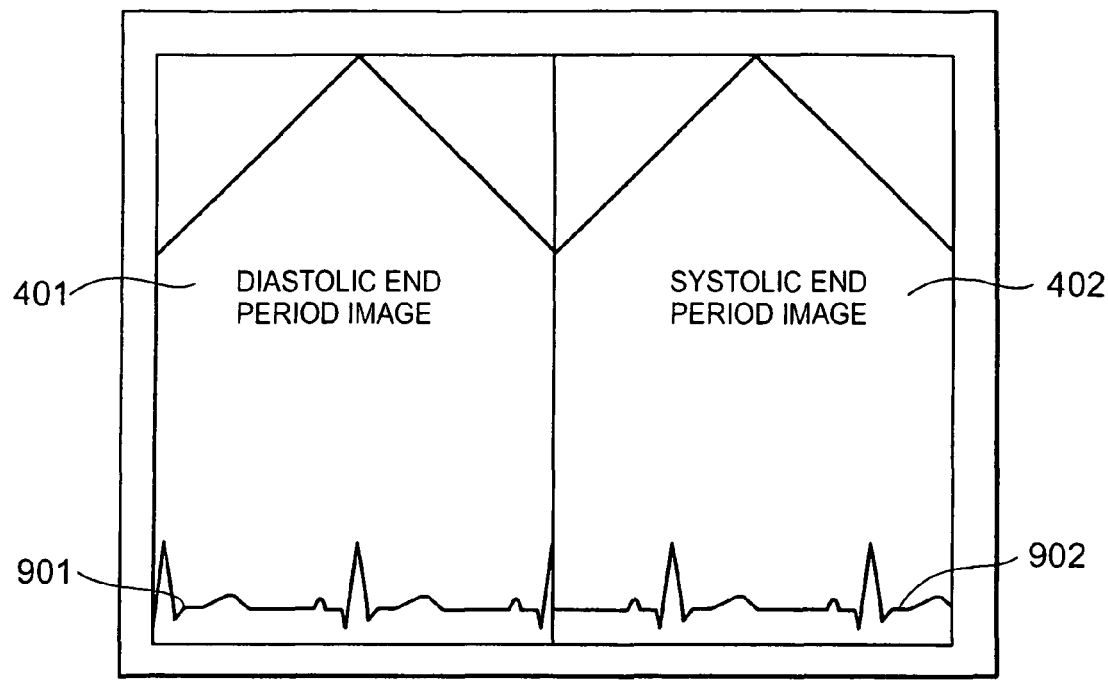
FIG. 9 illustrates a first exemplary dual display of images of a diastolic end period and a systolic end period.

FIG. 9 illustrates a first display manner for a dual display of a diastolic end period image and a systolic end period image. In FIG. 9, a diastolic end period image 401 and an electrocardiogram 901 centering a time point corresponded to the position of the image frame are displayed together. Similarly, a systolic end period image 402 and an electrocardiogram 902 centering a time point corresponded to the position of the image frame are displayed together.

As shown in FIG. 9, by displaying an electrocardiogram together with images, it becomes easier for an operator to diagnose or observe images with considering a relationship to the wave of the electrocardiogram.

Figure 10:
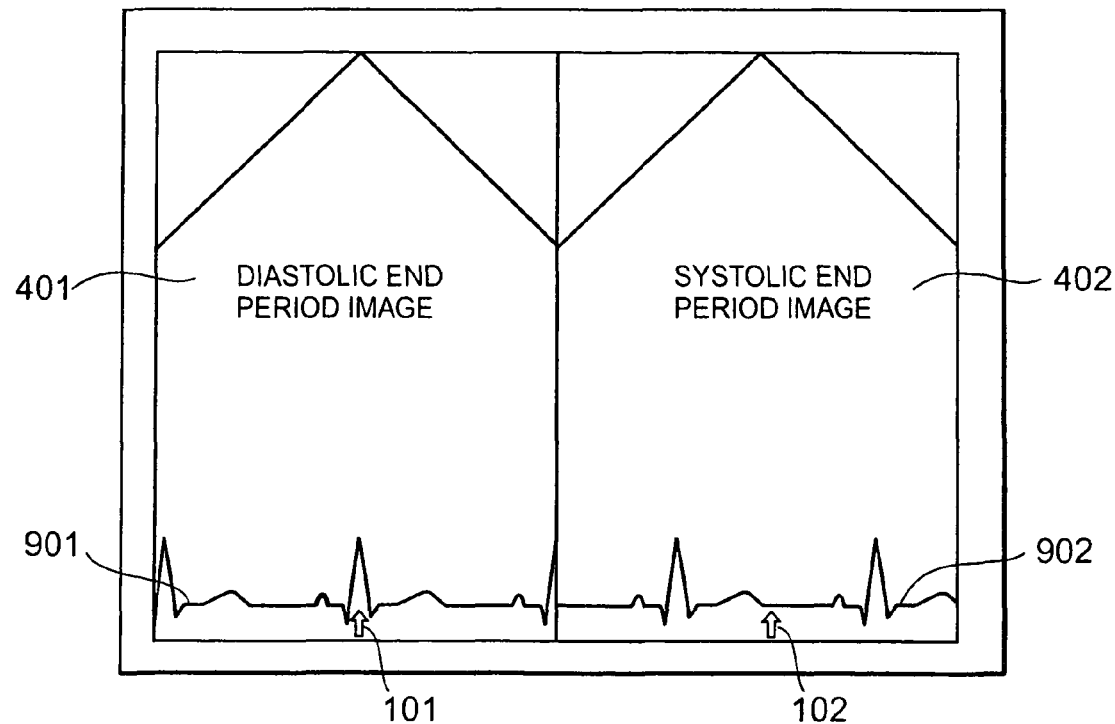
FIG. 10 illustrates a second exemplary dual display of images of a diastolic end period and a systolic end period.

FIG. 10 illustrates a second display manner for a dual display of a diastolic end period image and a systolic end period image. In FIG. 10, when a diastolic end period image 401 and an electrocardiogram 901 or a systolic end period image 402 and an electrocardiogram 902 are respectively displayed, marks 101 and 102 that respectively indicate each time point corresponded to each of end period image frames are displayed.

By displaying such marks on an electrocardiogram, an operator can easily understand the time point on the electrocardiogram for the displayed image.

Figure 11:
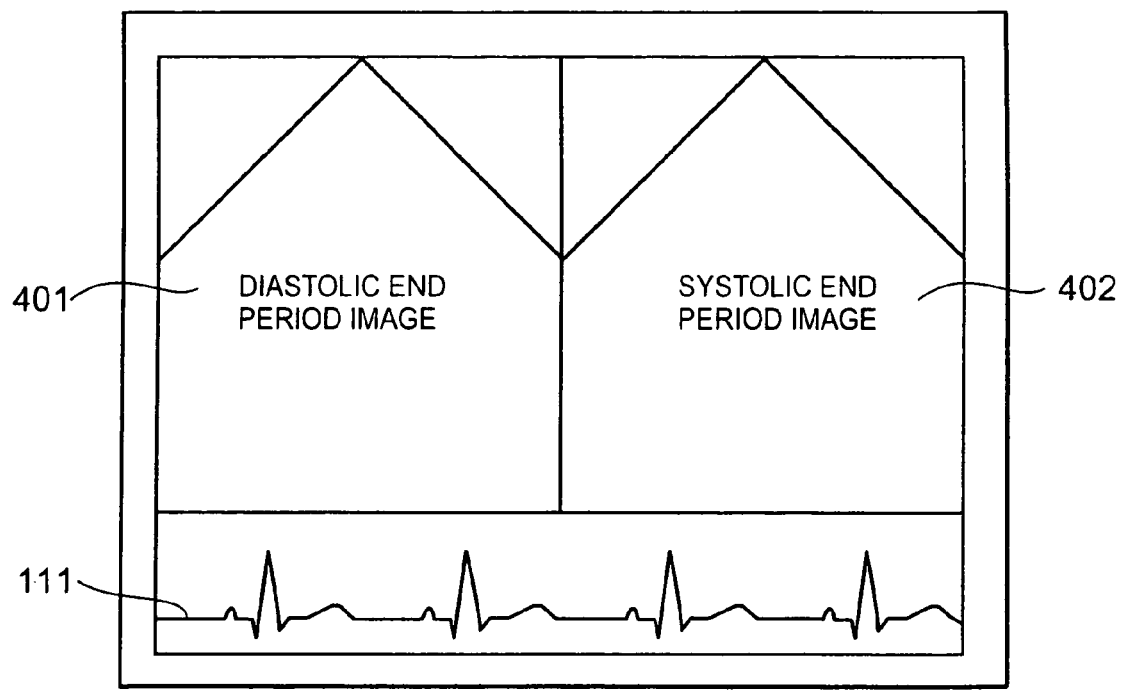
FIG. 11 illustrates a third exemplary dual display of images of a diastolic end period and a systolic end period.

FIG. 11 illustrates a third display manner for a dual display of a diastolic end period image and a systolic end period image. In FIG. 11, a common electrocardiogram 111 is displayed for a diastolic end period image 401 and a systolic end period image 402. It is also possible to display a mark as shown in FIG. 10 on the common electrocardiogram 111.

Figure 12:
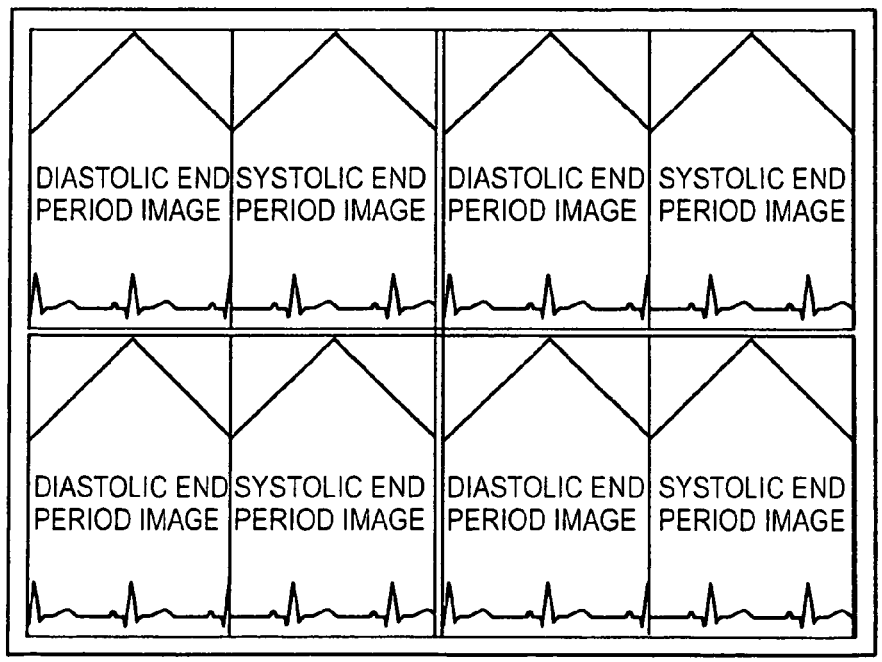
FIG. 12 illustrates a fourth exemplary dual display of images of a diastolic end period and a systolic end period.

FIG. 12 illustrates a fourth display manner for a dual display of a diastolic end period image and a systolic end period image. In FIG. 12, four pairs of a diastolic end period image and a systolic end period image are displayed at the same time.

In the step S31 in FIG. 2, when steps S26 to S30 are repeated by an input of an instruction of a dual display of a diastolic end period image and a systolic end period image at another heart cycle, the applicable pair of images is successively displayed. For example, initially image frames corresponding to the latest diastolic end period and the latest systolic end period that are searched by going back from a timing of the instruction input at step S24 are displayed at a left upper position, the next image pair in response to an instruction input at step S31 is displayed at a right upper position. The following image pair in response to a following input is displayed at a left lower position. When a further following instruction is input, an image pair in response to that further instruction is displayed at a right lower position. If a fifth instruction is input, each one screen is shifted on the display so as to display the latest image pair in response so that the latest input always appears at a right lower position. It is also possible to scroll for more than five image pairs by using the input unit 7. It is possible to apply another displaying method. The number of screens is not limited to four.

As shown in FIGS. 9 to 12, when the electrocardiogram is displayed, an input of an instruction for a dual display of a diastolic end period image and a systolic end period image belonging to another heart cycle as shown in step S31 in the flowcharts shown in FIG. 2 and FIGS. 6 to 8 can be performed by clicking on one point on the electrocardiogram.

Figure 13:
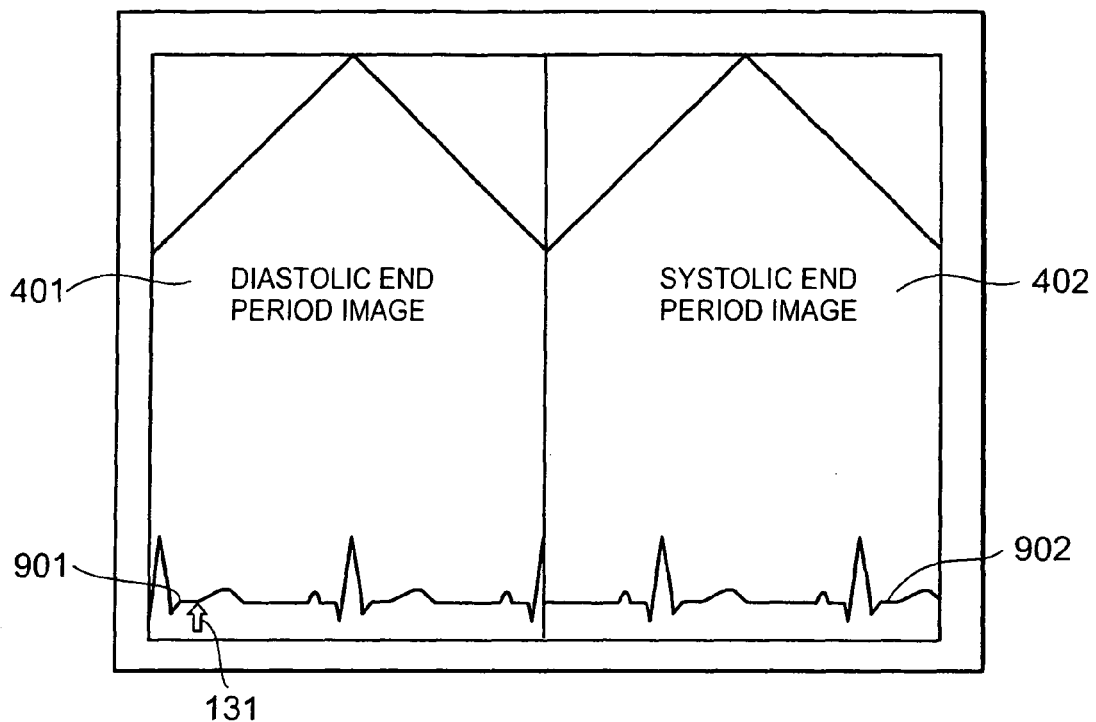
FIG. 13 illustrates another example for inputting an instruction for displaying a dual display of a diastolic end period image and a systolic end period image corresponded to another heart cycle on an electrocardiogram.

FIG. 13 illustrates an example when an instruction for dual display of a diastolic end period image and a systolic end period image belonging in another heart cycle is input on the displayed electrocardiogram. As shown in FIG. 13, an operator moves a cursor 131 on one point of the electrocardiogram 901 that is displayed together with a diastolic end period image 401 or one point on the electrocardiogram 902 that is displayed together with an end period image 402. By clicking at this point of the cursor position, image frames corresponding to a diastolic end period and a systolic end period that belong in a heart cycle including a clicking time point can be displayed through steps S26 to S28.

In the above embodiments, electrocardiogram data is used for searching for a diastolic end period and a systolic end period. However, even if electrocardiogram data is not used, it is possible to display images corresponding to a diastolic end period and a systolic end period by applying a measuring process through processor 29. Thus, the processor 29 performs a measuring process for each frame for an ultrasound image to recognize based on a result of the measuring process. By doing so, a diastolic end period image and a systolic end period image can be displayed without taking electrocardiogram data.

The present invention has been explained as an ultrasound image diagnosis apparatus. However, by eliminating processes relating to a real time display operation, the present invention is applicable to other image displaying apparatuses.

Figure 14:
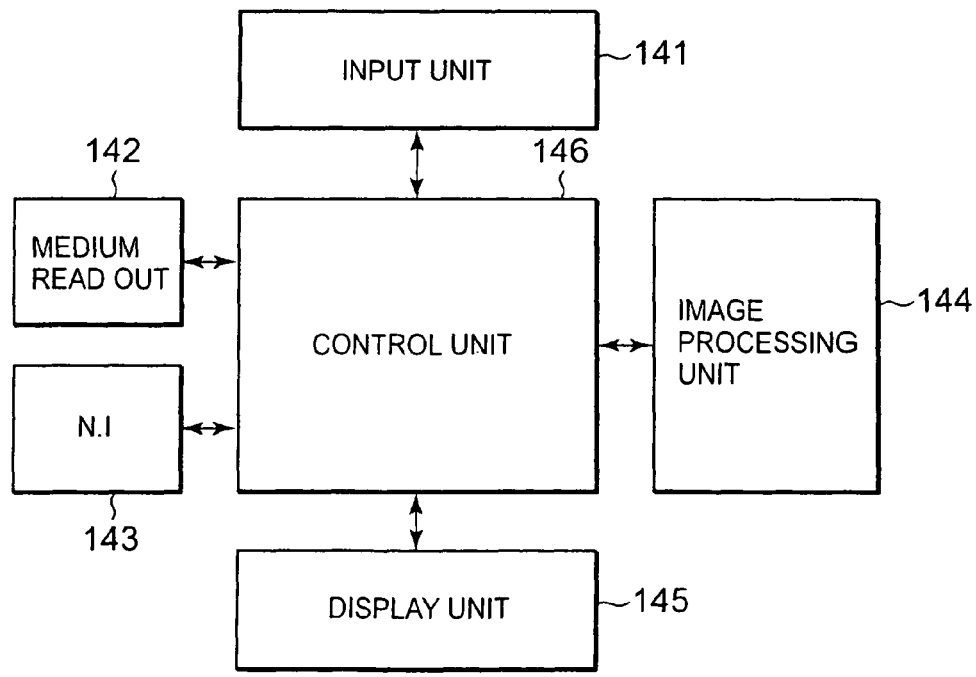
FIG. 14 is a block diagram illustrating an ultrasound image diagnosis apparatus of a second embodiment according to the present invention.

FIG. 14 is a block diagram illustrating an example of another image displaying apparatus consistent with the present invention. The image displaying apparatus includes an input unit 141 that can perform input operations similar to the above explained ultrasound image diagnosis apparatus, a recording medium reading unit 142 that can read out ultrasound images recorded in a recording medium, such as a disk, a network interface (N.I.) 143 that can read the ultrasound images collected by an ultrasound image diagnosis apparatus through a network, an image processing unit 144 for storing and processing the read images, a display unit 145 for displaying a diastolic end period image and a systolic end period image among the read ultrasound images, and a control unit 146 for controlling each of the units in the apparatus. Electrocardiogram data is basically acquired accompanying the ultrasound images acquired through the recording medium reading unit 142 or the network interface 143. It is, of course, possible to independently acquire the electrocardiogram data from the ultrasound images through recording medium reading unit 142 or the network interface 143 with keeping synchronization between the electrocardiogram data and the images. Electrocardiogram data is not always necessary. The image processing unit 144 can perform a measuring process against each frame of ultrasound images and can recognize images corresponding to each of a diastolic end period and a systolic end period based on the measuring process.

After reading the ultrasound images and electrocardiogram data into the image displaying apparatus, similar processes as explained in the above embodiments in FIGS. 2 and 8 can be performed.

Other embodiments consistent with the present invention will be apparent to those skilled in the art from consideration of the specification and practice of the present invention disclosed herein. It is intended that the specification and examples be considered as exemplary only, with a true scope and spirit of the present invention being indicated by the following claims.

The invention claimed is:

1. An ultrasound image diagnosis apparatus comprising:
a transmitting and receiving unit configured to transmit and receive ultrasound to and from an object;
a memory unit configured to store a plurality of ultrasound images in image frames acquired through transmission and reception of the ultrasound with a relation to living body signal data acquired through a living body signal measuring unit;

an input unit configured to receive input instructions from an operator;

a display unit configured to display the plurality of ultrasound images; and a display control unit configured to display images corresponding to each of a cardiac diastolic end period and a cardiac systolic end period by reading out respective ultrasound image frames from the memory unit based on the living body signal data in accordance with an input of a freeze command through the input unit during a display of the ultrasound image, by searching back from an acquisition time of the displayed image from a time of input of the freeze command for a latest diastolic end period image and a latest systolic end period image relative to that time of input of the freeze command.

2. The ultrasound image diagnosis apparatus according to claim 1, wherein the display control unit detects the diastolic end period by searching back on the living body signal data from the time of input of the freeze command; and the display control unit detects the systolic end period at a position just prior to the detected diastolic end period.

3. The ultrasound image diagnosis apparatus according to claim 1, wherein the display control unit detects a pair of a latest diastolic end period image frame and a latest systolic end period image frame by searching back from an optional operation time of the input of the freeze command;

the display control unit detects the latest diastolic end period image frame by searching back from the freeze command; and the display control unit detects the latest systolic end period at a position just prior to the detected latest diastolic end period.

4. The ultrasound image diagnosis apparatus according to claim 1, wherein each of the plurality of ultrasound image frames are stored in the memory unit in correspondence to timing points on the living body signal data.

5. The ultrasound image diagnosis apparatus according to claim 1, wherein the memory unit stores each of the ultrasound image frames in correspondence to a systolic end period and a diastolic end period based on the living body signal data.

6. The ultrasound image diagnosis apparatus according to claim 1, wherein the memory unit stores latest ultrasound image frames in correspondence to a latest systolic end period and a latest diastolic end period based on the living body signal data.

7. The ultrasound image diagnosis apparatus according to claim 1, wherein the display control unit reads out the ultrasound image frames and the living body signal data stored in the memory unit and judges each of a systolic end period and a diastolic end period based on a timing of synchronization between the ultrasound transmission and reception and the living body signal data.

8. The ultrasound image diagnosis apparatus according to claim 1, wherein the display control unit automatically displays the respective reproduction images of the ultrasound image frames corresponded to each of the systolic end period and the diastolic end period as a dual display on a screen of the display unit.

9. The ultrasound image diagnosis apparatus according to claim 1, wherein the display control unit reads image frames corresponded to the respective systolic end period and diastolic end period that belong to a heart cycle including a desired position from the memory unit, and displays the read image frames on the display when the input of the freeze command is given at a desired position on the living body signal data displayed on the display and an instruction for displaying end period images is input.

10. The ultrasound image diagnosis apparatus according to claim 1, wherein the display control unit reads out image frames corresponded to each of a systolic end period and a diastolic end period in a heart cycle detected by searching back a predetermined number of heart cycles from the heart cycle of the systolic end period and the diastolic end period from the memory unit, and displays the read image frames on the display in accordance with a position instructing input on the living body signal data through the input unit, when the display unit displays the image frames corresponded to the respective systolic end period and diastolic end period on the display.

11. The ultrasound image diagnosis apparatus according to claim 1, wherein the display control unit searches back a certain number of heart cycles on the living body signal data in accordance with an instruction input of a position an the living body signal data and displays a pair of image frames that correspond to the systolic end period and diastolic end period in the heart cycle.

12. The ultrasound image diagnosis apparatus according to claim 11, wherein the instruction input of the position on the living body signal data is determined as a prescribed number of the heart cycles.

13. The ultrasound image diagnosis apparatus according to claim 11, wherein the image processing unit searches back a prescribed number of heart cycles on the living body signal data in accordance with repetition of instruction inputs of positions through the input unit, and searches back a prescribed number of heart cycles so as to display a pair of image frames that belong to the systolic end period and the diastolic end period of the heart cycle.

14. The ultrasound image diagnosis apparatus according to claim 1, wherein the input of the freeze command is supplied through the input unit during a display of the ultrasound images in real time, and the display control unit searches for a cardiac systolic end period or a cardiac diastolic end period by searching back on the stored living body signal data from a point that corresponds to the displayed image frames at a time of the input of the freeze command to display ultrasound image frames corresponded to the searched end periods on the display.

15. The ultrasound image diagnosis apparatus according to claim 1, wherein the input of the freeze command is supplied when one frame among the plurality of image frames is statistically displayed; and the display control unit searches for a cardiac systolic end period or a cardiac diastolic end period by searching back on the stored living body signal data from a point that corresponds to the displayed image frames at a time of the input of the freeze command to display ultrasound image frames corresponded to the searched end periods on the display.

16. The ultrasound image diagnosis apparatus according to claim 1, wherein the display control unit searches for a pair of latest image frames corresponded to each of a latest systolic end period and a latest diastolic end period by searching back from the freeze input and also searches for a plurality of pairs of images of a systolic end period and a diastolic end period corresponded to each of a plurality of heart cycles searching back from each of the latest end periods; and the display unit displays the plurality of pairs of images of the searched systolic end period and diastolic end period with the pair of latest image frames of the systolic end period and the diastolic end period.

17. The ultrasound image diagnosis apparatus according to claim 1, wherein the display control unit performs a search of latest image frames of the systolic end period and diastolic end period by searching back on the living body signal data from an input position to find latest images corresponded to each of the systolic end period and diastolic end period.

18. The ultrasound image diagnosis apparatus according to claim 1, wherein the display control unit performs image display as a real time display of images through the transmitting and receiving unit.

19. The ultrasound image diagnosis apparatus according to claim 1, wherein the display control unit performs image display by reproducing image frames stored in the memory unit.

20. An image display processing apparatus comprising:
a reading unit configured to read out ultrasound images including plurality of image frames and living body signal data;
a memory configured to store the read ultrasound images in correspondence to the living body signal data;
an input unit configured to receive input instructions from an operator including a freeze input;
a display unit configured to display images; and
a display control unit configured to search for image frames corresponding to each of a latest cardiac systolic end period and a latest diastolic end period in the memory, by searching back on the living body signal data from a time point of the freeze input to display the searched images of the latest systolic end period and the latest diastolic end period on the display relative to that time point of the freeze input.

21. The image display processing apparatus according to claim 20, wherein the reading unit reads the image frames through a network.

22. The image display processing apparatus according to claim 20, wherein the reading unit reads the image frames from a data recording medium.

23. A method for processing an ultrasound image display comprising:
transmitting and receiving ultrasound;
measuring living body signals;
storing a plurality of image frames collected by the transmission and reception in correspondence to living body signal data collected by the measuring;
inputting a freeze input;
searching for a cardiac systolic end period image or a cardiac diastolic end period image based on the living body signal data, by searching back from a time of the freeze input for a latest diastolic end period image and a latest systolic end period image relative to that time of the freeze input; and
displaying at least one of the searched cardiac systolic end period image or the searched cardiac diastolic end period image on a screen.

24. The method for processing image display according to claim 23, wherein a latest cardiac systolic end period image and a latest cardiac diastolic end period image are displayed as a dual display.

25. The method for processing image display according to claim 23, wherein the living body signal is electrocardiogram data; and
the cardiac systolic end period and diastolic end period are displayed together with each corresponded to the electrocardiogram data.

26. The method for processing image display according to claim 23, further comprising:
inputting a release instruction for releasing the freeze input; and
returning to displaying reproduction images in real time from static image displays of the systolic end period and diastolic end period.

27. The method for processing image display according to claim 23, wherein the searching is performed so as to find a desired cardiac systolic end period image frame and a desired cardiac diastolic end period image among the stored image frames by searching back from a timing of the freeze input operation; and further comprising:
displaying searched image frames of the desired cardiac systolic end period and the desired cardiac diastolic end period as dual static images.

28. The method for processing image display according to claim 27, further comprising:
judging no existence of the searched for desired cardiac systolic end period image frame and the searched for desired cardiac diastolic end period image frame among the stored image frames; and
displaying no display or an error message when the judging judges that no desired images exist.

29. The method for processing image display according to claim 27, wherein the searching of image frames of the systolic end period image frame and the diastolic end period image frame is performed based on another heart cycle or a preliminary designated heart cycle being input through an input unit.

30. The method for processing image display according to claim 29, wherein the preliminary designated heart cycle is an optional designated heart cycle; and further comprising:
changing the optional designated heart cycle during display of the systolic end period image and diastolic end period image.

* * * * *